United States Patent [19]
Ruben

[11] 4,225,667
[45] Sep. 30, 1980

[54] DENTAL APPLIANCE

[76] Inventor: Philip H. Ruben, 9201 Sunset Blvd., Suite 903, Los Angeles, Calif. 90069

[21] Appl. No.: 970,327

[22] Filed: Dec. 18, 1978

[51] Int. Cl.² .............................................. A61C 3/00
[52] U.S. Cl. .................................... 433/162; 433/82; 128/321
[58] Field of Search ............... 32/40 R, 19, 22, 17; 128/321, 322; 433/162, 82

[56] References Cited

U.S. PATENT DOCUMENTS

| | | | |
|---|---|---|---|
| 1,439,022 | 12/1922 | Quilling | 32/40 R |
| 3,916,909 | 11/1975 | Kletschka et al. | 128/321 |
| 3,980,086 | 9/1976 | Kletschka et al. | 128/321 |

FOREIGN PATENT DOCUMENTS 932982  7/1963  United Kingdom ............... 128/321

OTHER PUBLICATIONS

"Miller Articulating Paper Forcep" ad, Silverman's catalog, 1976, p. 74.

Primary Examiner—Louis G. Mancene
Assistant Examiner—John J. Wilson
Attorney, Agent, or Firm—Charles H. Schwartz

[57] ABSTRACT

A dental appliance for supporting marking paper within a patient's mouth and for directing a supply of air toward the marking paper, including first means for holding marking paper for insertion into a patient's mouth between opposing tooth surfaces, the first means including jaw members for holding the marking paper and additionally including means for opening the jaw members for releasing the marking paper, and second means operatively coupled to the jaw members for receiving and directing a supply of air toward the marking paper for maintaining the marking paper and the opposing tooth surfaces dry.

10 Claims, 9 Drawing Figures

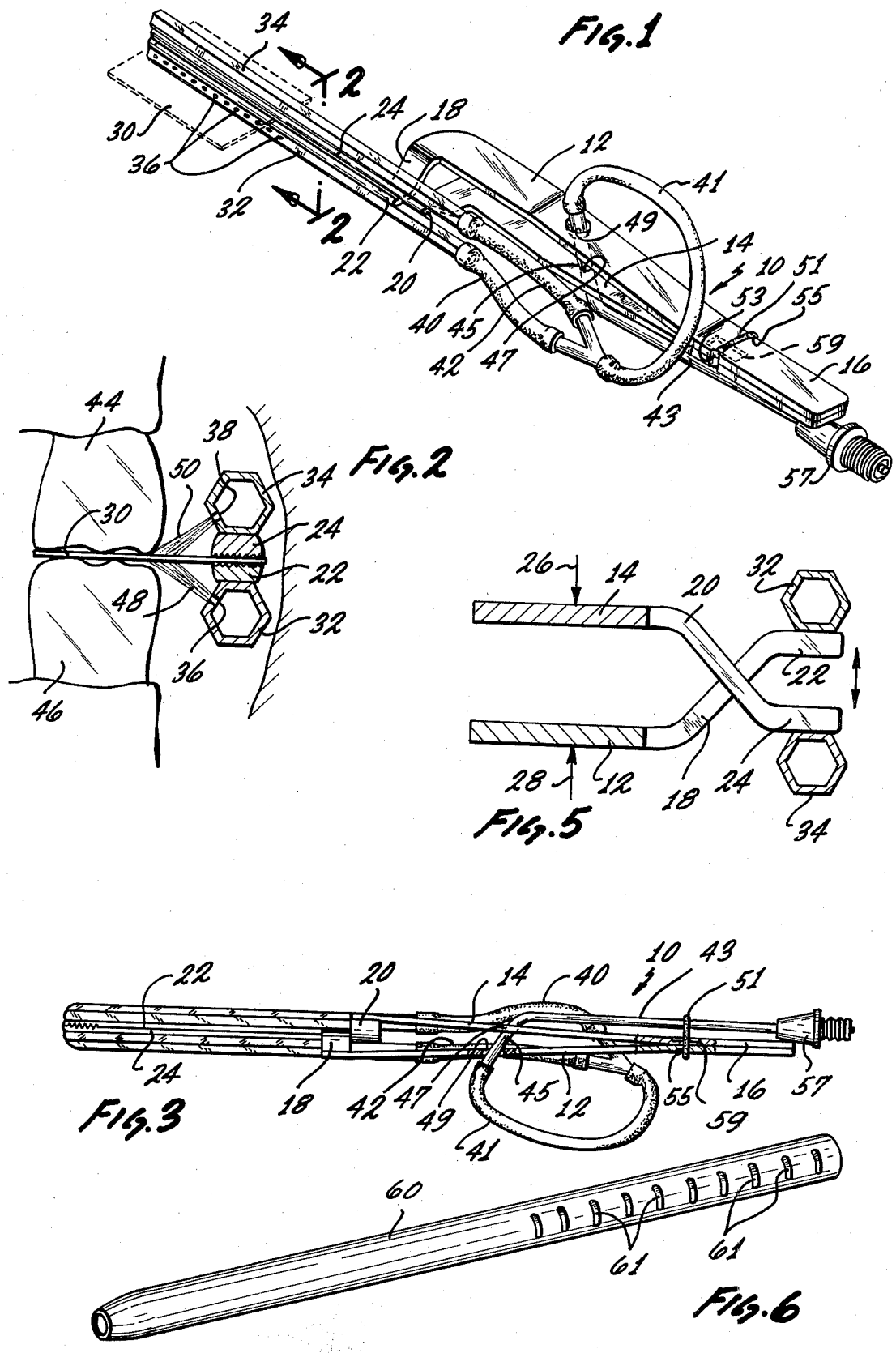

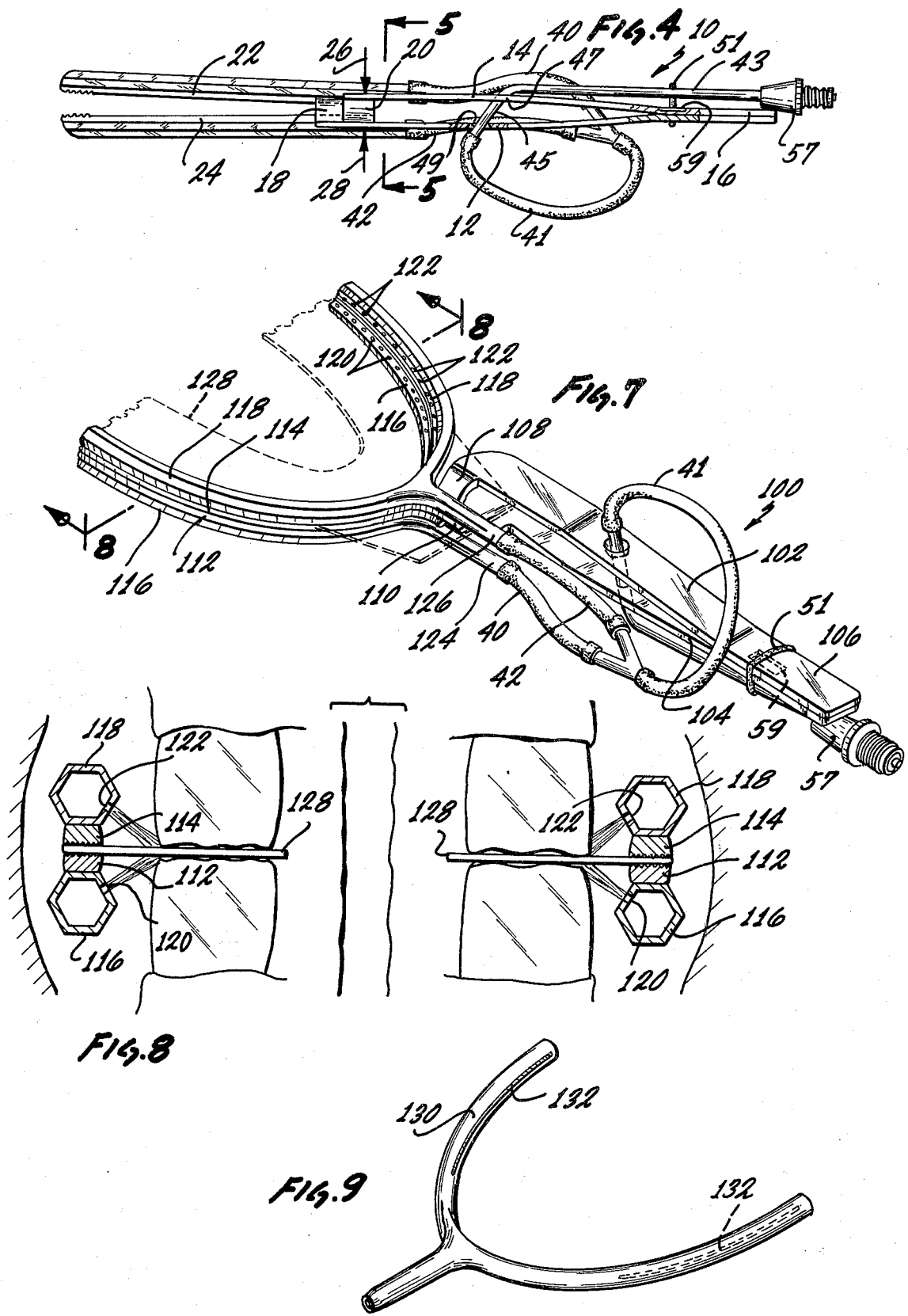

DENTAL APPLIANCE

The present invention is directed to a dental appliance for supporting marking paper and for directing air toward the marking paper within a patient's mouth, and for making a marking, using marking paper, of the biting surface of the patient's teeth.

As part of the procedures practiced by a dentist, it is often desirable to make a marking using special marking paper of the biting surfaces between opposing teeth. For example, after filling a tooth or inserting a crown or a bridge or with fitting a plate, it is necessary to insure that the contact between opposing teeth provides for a proper bite. This is necessary for the patient's comfort as well as insuring that there is no improper contact between opposing teeth which could cause pressure and pain to the patient.

In order to determine the contact between opposing teeth, dentists use various types of marking paper which provide for a marking which represent the contact between the opposing teeth. For example, the paper may have one surface similar to carbon paper and provides for marking on one tooth of the contact points from the other opposing tooth. In addition, the marking may be provided on a separate piece of paper instead of on the opposing tooth and may actually be provided from the opposing teeth on both sides of a separate piece of paper sandwiched between two pieces of marking paper.

In order to insure that the markings are retained in position on the tooth or on the paper, it is desirable to maintain the surrounding areas of the teeth dry so that the patient's saliva will not obliterate the markings. The present invention is directed to a dental appliance which serves a dual function of holding the marking paper in position for providing the marking either on a tooth surface or on a separate piece of paper and with the appliance also including means for providing a flow of air to both sides of the paper and toward the opposing surfaces of the teeth to maintain the paper and the opposing surfaces of the teeth dry during the marking procedure. The dental appliance of the present invention also includes means for supporting an air supply tube so that the tube is held in position but is movable to aid in positioning the dental appliance within the patient's mouth.

The dental appliance of the present invention in one embodiment provides for holding the paper and supplying the air along one side of the mouth. A second embodiment of the invention provides for holding the paper and supplying air for the complete mouth.

A clearer understanding of the invention will be had with reference to the following description and drawings wherein FIG. 1 illustrates a perspective view of a dental appliance of the present invention;

FIG. 2 illustrates the dental appliance of FIG. 1 taken along lines 2—2 of FIG. 1 and with the dental appliance shown within the mouth and adjacent opposing teeth;

FIG. 3 is a side view of the dental appliance of FIG. 1 in a closed position;

FIG. 4 is a side view of the dental appliance of FIG. 1 in an open position;

FIG. 5 is an enlarged cross-sectional view of the dental appliance taken along lines 5—5 of FIG. 4;

FIG. 6 is a view of an alternative structure for the air supply members of the appliance of FIG. 1;

FIG. 7 is a perspective view of a second embodiment of the dental appliance of the present invention;

FIG. 8 is a cross-sectional view taken along lines 8—8 of FIG. 7 of the dental appliance of FIG. 7 and shown within a mouth of a patient; and FIG. 9 is a view of an alternative structure for the air supply members of the second embodiment of the dental appliance of the present invention.

In FIG. 1, the first embodiment of the appliance of the present invention is shown to include a tweezer member 10 which consists of a pair of resilient spring portions 12 and 14 connected together at end 16. The ends of the resilient portions 12 and 14 include intermediate bent portions 18 and 20 which are at right angles to the main body of the resilient members 12 and 14. The bent portions 18 and 20 overlie each other so that when the resilient portions 12 and 14 are squeezed together the ends of the portions 18 and 20 are spread apart. Extending from the ends of the portions 18 and 20 are elongated jaw portions 22 and 24.

The relationship between the various portions of the tweezer 10 in the closed and open positions may be seen in FIGS. 3, 4 and 5 where in in FIG. 3 the jaw portions 22 and 24 are together and in FIGS. 4 and 5 the jaw portions 22 and 24 are spread apart. The jaw portions are spread apart on the application of force as shown by the arrows 26 and 28 in FIGS. 4 and 5. As shown in FIG. 1, paper such as a carbon paper 30 may be retained between the jaw portions 22 and 24. This may also be seen in FIG. 2 which shows the jaw portions 22 and 24 supporting the paper 30 within the mouth of a patient.

Supported on the jaw portions 22 and 24 are a pair of elongated air supply members 32 and 34. The air supply members 32 and 34 include a plurality of openings such as the openings 36 in member 32 and openings 38 in member 34. In place of the plurality of small openings an elongated slot may also be used. Each of the air supply members 32 and 34 are tubular, and are open at one end to receive a supply of air, and are closed at the other end so that the air flows from the plurality of openings 36 and 38. For example, flexible air supply tubes 40 and 42 are coupled to the open ends and supply air to the tubular members. It is to be appreciated that each jaw portion and its associated tubular member may be formed as an integral member instead of the two joined members.

The flexible air supply tubes 40 and 42 are coupled together to form a single flexible air supply tube 41. In order to supply air to the dental appliance of the present invention, a rigid air tube 43 may be positioned along the length of the resilient members 12 and 14. The end 45 of the air tube 43 is normally bent and openings 47 and 49 in the resilient members 14 and 12 are offset to hold the end 45 in position. The opening 49 is also tapered to tend to lock the end of the flexible tube 41 on the end 45 of the air tube 43 if the air tube 43 is moved to pull the tube 41 into the opening 49.

A flexible band 51 fits in notches 53 and 55 and holds the tube 43 in position. A connector 57 is used to connect the air tube 43 to a standard air syringe used by dentists. A groove 59 allows for the end 45 of the tube 43 to be inserted under the flexible band 51. This type of mounting provides for the air tube 43 to be locked in position but still allows for freedom of movement of the air tube 43 to aid in positioning the dental appliance within the patient's mouth.

As shown in FIG. 2, the dental appliance may be positioned within the patient's mouth to have the paper 30 lie between opposing teeth 44 and 46. The flow of air is directed from the openings 36 and 38 as shown by the air streams 48 and 50 to keep the paper 30 dry and to enter the space between the opposing teeth 44 and 46 to keep these opposing surfaces dry. As the patient bites down, marks are made from the paper 30 from one tooth surface to a marking surface. The marking surface may be the other of the opposing teeth if the paper 30 is a single piece of marking paper. Alternatively, the paper 30 may be formed as a sandwich of either a piece of marking paper and a blank piece of paper, or two pieces of marking paper and an intermediate piece of blank paper so as to provide for the desired markings for the dentist's use.

FIG. 5 illustrates an enlarged cross-sectional view taken along lines 5—5 of FIG. 4 and shows how the tweezer portions 22 and 24 may be spread apart by pressing down on the portions 12 and 14. FIG. 6 illustrates an alternative structure for the air supply tubes such as air supply tube 60 and shows the tube to be round and slots 61 used in place of the openings 36. As indicated above, in place of the plurality of openings 36 or slots 61, an elongated slot may be used. Also, the air supply tube may be integral with its associated jaw portion 22.

FIG. 7 illustrates a second embodiment of the invention which provides for the dental appliance being used for both sides of the patient's mouth. In FIG. 7, a tweezer 100 includes flexible members 102 and 104 connected together at end 106. Intermediate overlying bent members 108 and 110 operate in a similar manner to the embodiment shown in FIG. 1 and as the flexible portions 102 and 104 are pressed together, the ends of the members 108 and 110 are spread apart.

Extending from the ends of the portions 108 and 110 are U-shaped jaw portions 112 and 114. The U-shaped portions support U-shaped air supply members 116 and 118. The entire U-shaped structure including the tweezer portions and the air supply members will fit within the patient's mouth to either side of the teeth as shown in FIG. 8.

The air supply members 116 and 118 are tubular and include openings 120 in member 116 and openings 122 in member 118 so as to supply air around both sides of the patient's mouth. The air supply members 116 and 118 also include tubular tip portions 124 and 126 to which a supply of air is connected such as through the use of the flexible tubes 40 and 42 and the use of associated structure as shown in FIGS. 1, 3 and 4.

The dental appliance of FIG. 7 may be spread apart to receive the marking paper 128. This paper 128 also has a U-shape and, as seen in FIG. 8, the paper 128 may be positioned between opposing teeth on both sides of the patient's mouth. This enables the dentist to provide for a complete bite pattern, using the marking paper.

FIG. 9 illustrates an alternative structure for the air supply members such as member 130 and shows an elongated slot 132 in place of the plurality of openings 120. As can be seen in FIG. 8, the openings 120 in member 116 and the openings 122 in member 118 are positioned so that the air streams as shown in FIG. 8 are directed to the marking paper 128 and also to the flow between the opposing surfaces of the teeth. The elongated slot 132 would operate in a similar fashion. In this way, the paper and the opposing surfaces of the teeth are kept dry so as not to obliterate the marking which is desired by the dentist.

Although the invention has been described with reference to particular embodiments, it is to be appreciated that various adaptations and modifications may be made and the invention is only to be limited by the appended claims.

I claim:

1. A dental appliance for holding marking paper for use in making a marking of a patient's bite, including,
    a tweezer member, including a pair of resilient portions and a pair of opposing jaw portions for receiving and supporting the marking paper and with intermediate means interconnecting each jaw portion with one of the resilient portions,
    the jaw portions maintained by the resilient portions in a normally closed position for supporting the marking paper and with the jaw portions in an open position for receiving the marking paper in accordance with the resilient portions moved toward each other,
    at least one air supply means operatively coupled to one of the jaw portions for directing a supply of air toward the marking paper when supported by the jaw portions, and
    ;the air supply means formed as an elongated tubular member open at one end and closed at the other end having at least one opening along its length for directing air supplied from the open end.

2. The dental appliance of claim 1 wherein the tubular member has a plurality of openings along its length.

3. The dental appliance of claim 1 wherein the tubular member is formed as a U-shaped member having closed ends and an opening intermediate the closed ends for receiving air and with additional openings along both portions of the U-shaped member for directing air from both portions of the U-shaped member.

4. A dental appliance for supporting marking paper within a patient's mouth and for directing a supply of air toward the marking paper, including,
    first means for holding marking paper for insertion into a patient's mouth between opposing tooth surfaces,
    the first means including jaw members for holding the marking paper and additionally including means for opening the jaw members for releasing the marking paper,
    second means operatively coupled to the jaw members for receiving and directing a supply of air toward the marking paper for maintaining the marking paper and the opposing tooth surfaces dry, and
    the second means formed as an elongated tubular member open at one end and closed at the other end having at least one opening along its length for directing air supplied from the open end.

5. The dental appliance of claim 4 wherein the tubular member has a plurality of openings along its length.

6. The dental appliance of claim 4 wherein the tubular member is formed as a U-shaped member having closed ends and an opening intermediate the closed ends for receiving air and with additional openings along both portions of the U-shaped member for directing air from both portions of the U-shaped member.

7. A dental appliance for holding marking paper for use in making a marking of a patient's bite, including,
    a tweezer member, including a pair of resilient portions and a pair of opposing jaw portions for receiving and supporting the marking paper and with intermediate means interconnecting each jaw portion with one of the resilient portions, the jaw portions maintained by the resilient portions in a normally closed position for supporting the marking paper and with the jaw portions in an open position for receiving the marking paper in accordance with the resilient portions moved toward each other, and two air supply means individually operatively coupled to the pair of the jaw portions for directing a supply of air toward opposite sides of the marking paper when supported by the jaw portions.

8. A dental appliance for supporting marking paper within a patient's mouth and for directing a supply of air toward the marking paper, including, first means for holding marking paper for insertion into a patient's mouth between opposing tooth surfaces, the first means including jaw members for holding the marking paper and additionally including means for opening the jaw members for releasing the marking paper and wherein the means additionally included in the first means is formed from resilient members which maintain the jaw members in a normally closed position, second means operatively coupled to the jaw members for receiving and directing a supply of air toward the marking paper for maintaining the marking paper and the opposing tooth surfaces dry, and the second means including air supply means individually operatively coupled to the jaw members for directing a supply of air toward opposite sides of the marking paper.

9. A dental appliance for holding marking paper for use in making a marking of a patient's bite, including, a tweezer member, including a pair of resilient portions and a pair of opposing jaw portions for receiving and supporting the marking paper and with intermediate means interconnecting each jaw portion with one of the resilient portions, the jaw portions maintained by the resilient portions in a normally closed position for supporting the marking paper and with the jaw portions in an open position for receiving the marking paper in accordance with the resilient portions moved toward each other, at least one air supply means operatively coupled to one of the jaw portions for directing a supply of air toward the marking paper when supported by the jaw portions, a rigid air tube having a bent end and with the resilient portions including openings to receive the bent end and means for supporting the air tube adjacent the resilient portions and with means interconnecting the air tube and the air supply means, and the means for supporting the air tube including a flexible band passing around the air tube and the resilient portions and including notches in the resilient portions to receive the flexible band.

10. A dental appliance for supporting marking paper within a patient's mouth and for directing a supply of air toward the marking paper, including, first means for holding marking paper for inserting into a patient's mouth between opposing tooth surfaces, the first means including jaw members for holding the marking paper and additionally including means for opening the jaw members for releasing the marking paper, second means operatively coupled to the jaw members for receiving and directing a supply of air toward the marking paper for maintaining the marking paper and the opposing tooth surfaces dry, a rigid air tube having a bent end and with the resilient portions including openings to receive the bent end and means for supporting the air tube adjacent the resilient portions and with means interconnecting the air tube and the air supply means, and the means for supporting the air tube including a flexible band passing around the air tube and the resilient portions and including notches in the resilient portions to receive the flexible band.

* * * * *